US00PP36429P2

(12) United States Plant Patent
Hartman

(10) Patent No.: US PP36,429 P2
(45) Date of Patent: Feb. 4, 2025

(54) ***CALADIUM* PLANT NAMED 'WCH OF14-1172'**

(50) Latin Name: ***Caladium* X *hortulanum***
Varietal Denomination: WCH OF14-1172

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 18/657,779

(22) Filed: May 8, 2024

(51) Int. Cl.
*A01H 5/12* (2018.01)
*A01H 6/10* (2018.01)

(52) U.S. Cl.
USPC ..... Plt./373

(58) Field of Classification Search
USPC ..... Plt./373
CPC ..... A01H 5/12; A01H 5/00; A01H 6/10
See application file for complete search history.

(56) References Cited

U.S. PATENT DOCUMENTS

PP23,815 P2 * 8/2013 Hartman ..... A01H 6/10
Plt./373

* cited by examiner

*Primary Examiner* — June Hwu
(74) *Attorney, Agent, or Firm* — C. Anne Whealy

(57) ABSTRACT

A new and distinct cultivar of *Caladium* plant named 'WCH OF14-1172', characterized by its upright plant habit and intermediate to tall in height; dense, leafy and bushy appearance; vigorous growth habit and rapid growth rate; fancy-type leaves that are medium green and white in color with random and variable pink-colored blushes with darker green-colored margins and venation; and petioles that are close to black in color with tan, brown to almost black-colored stripes.

4 Drawing Sheets

Figure 1:
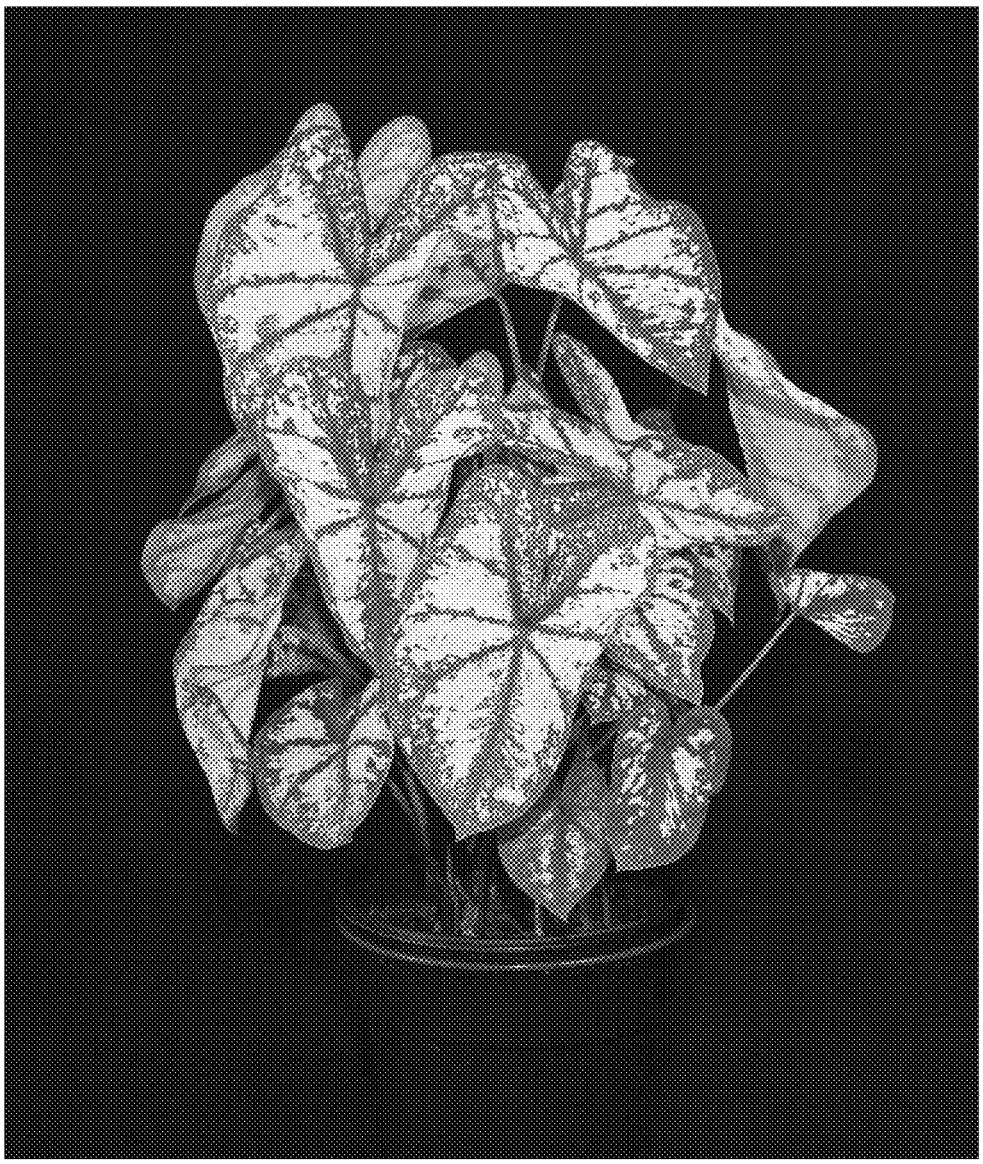

Botanical designation: *Caladium* X *hortulanum*.
Cultivar denomination: 'WCH OF14-1172'.

BACKGROUND OF THE INVENTION

The present invention relates to a new and distinct cultivar of *Caladium* plant, botanically known as *Caladium* X *hortulanum*, commercially referred to as a fancy leaf-type *Caladium* and hereinafter referred to by the name 'WCH OF14-1172'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April 2013 in Avon Park, Florida of *Caladium* X *hortulanum* 'White Christmas', not patented, as the female, or seed, parent with *Caladium* X *hortulanum* 'Monument', disclosed in U.S. Plant Pat. No. 27,948, as the male, or pollen, parent. The new *Caladium* plant was discovered and selected by the Inventor as a single plant within the progeny of the stated cross-pollination in a controlled outdoor nursery environment in Avon Park, Florida in September 2014.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Florida since April 2015 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'WCH OF14-1172'. These characteristics in combination distinguish 'WCH OF14-1172' as a new and distinct *Caladium* plant:

1. Upright plant habit and intermediate to tall in height; dense, leafy and bushy appearance.
2. Vigorous growth habit and rapid growth rate.
3. Fancy-type leaves that are medium green and white in color with random and variable pink-colored blushes with darker green-colored margins and venation.
4. Petioles that are close to black in color with tan, brown to almost black-colored stripes.

Plants of the new *Caladium* differ primarily from plants of the female parent, 'White Christmas', in the following characteristics:

1. Plants of the new *Caladium* are taller than plants of 'White Christmas'.
2. Plants of the new *Caladium* produce more tubers than plants of 'White Christmas'.
3. Leaves of plants of the new *Caladium* are medium green and white in color with random and variable pink-colored blushes with darker green-colored margins and venation whereas leaves of plants of 'White Christmas' have distinct dark green-colored venation with white-colored interveinal areas that are often tinged with pink and dark green-colored margins.
4. Petioles of plants of the new *Caladium* are close to black in color with tan, brown to almost black-colored stripes whereas petioles of plants of 'White Christmas' are green in color with almost black-colored stripes.

5. Plants of the new *Caladium* are more resistant to Bacterial Leafspot than plants of 'White Christmas'.

Plants of the new *Caladium* differ primarily from plants of the male parent, 'Monument', in the following characteristics:

1. Plants of the new *Caladium* are somewhat taller than plants of 'Monument'.
2. Leaves of plants of the new *Caladium* are medium green and white in color with random and variable pink-colored blushes with darker green-colored margins and venation whereas leaves of plants of 'Monument' have medium green-colored venation, white and/or white and pink-colored interveinal areas and green-colored areas marked with white or pink-colored flecks and speckles.
3. Petioles of plants of the new *Caladium* are close to black in color with tan, brown to almost black-colored stripes whereas petioles of plants of 'Monument' are tannish green in color blushed with lavender pink and with brownish green-colored streaks, stippling and tessellations.

Plants of the new *Caladium* can be compared to plants of *Caladium* X *hortulanum* 'White Cap', disclosed in U.S. Plant Pat. No. 23,815. In side-by-side comparisons, plants of the new *Caladium* differ primarily from plants of 'White Cap' in the following characteristics:

1. Leaves of plants of the new *Caladium* are medium green and white in color with random and variable pink-colored blushes with darker green-colored margins and venation whereas leaves of plants of 'White Cap' are medium green in color with white-colored venation surrounded by green-colored areas and white-colored interveinal blotches.
2. Petioles of plants of the new *Caladium* are close to black in color with tan, brown to almost black-colored stripes whereas petioles of plants of 'White Cap' are green, tan and brown in color.

Plants of the new *Caladium* can also be compared to plants of *Caladium* X *hortulanum* 'Candidum Senior', not patented. In side-by-side comparisons, plants of the new *Caladium* differ primarily from plants of 'Candidum Senior' in the following characteristics:

1. Plants of the new *Caladium* are taller and more upright than plants of 'Candidum Senior'.
2. Plants of the new *Caladium* produce more tubers than plants of 'White Christmas'.
3. Plants of the new *Caladium* produce larger and more rounded tubers than plants of 'White Christmas'.
4. Leaves of plants of the new *Caladium* are medium green and white in color with random and variable pink-colored blushes with darker green-colored margins and venation whereas leaves of plants of 'Candidum Senior' are greenish white in color with medium green-colored venation and thin green-colored margins.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'WCH OF14-1172' grown in a container that has had its tuber de-eyed prior to planting.

Figure 2:
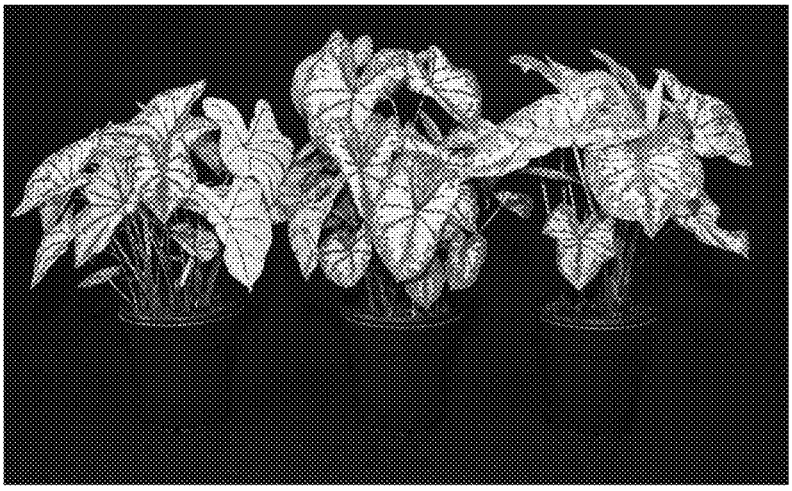

The photograph at the top of the second sheet (FIG. 2) is side perspective view of typical plants of the female parent, 'White Christmas' (left), 'WCH OF14-1172' (center) and the male parent, 'Monument' (right).

Figure 3:
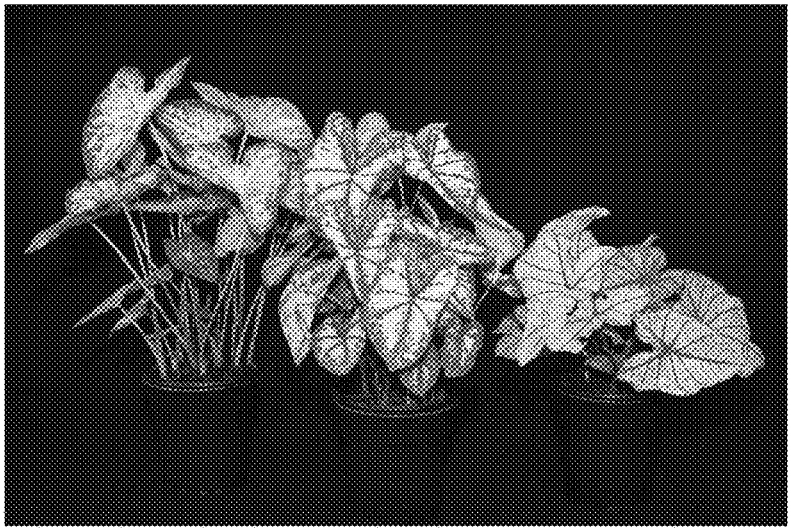

The photograph at the bottom of the second sheet (FIG. 3) is side perspective view of typical plants of 'White Cap' (left), 'WCH OF14-1172' (center) and 'Candidum Senior' (right).

Figure 4:
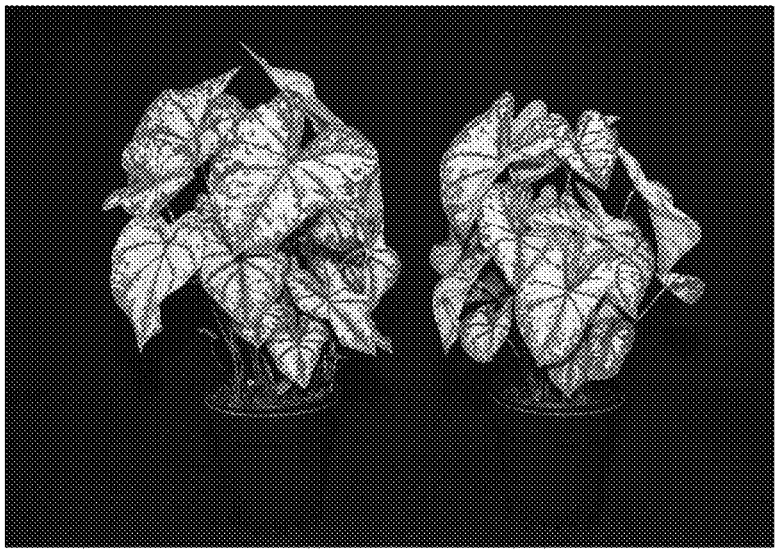

The photograph at the top of the third sheet (FIG. 4) is a comparison view of typical plants of 'WCH OF14-1172' grown in containers, the plant on the left has not had its tuber de-eyed and the plant on the right has had its tuber de-eyed prior to planting.

Figure 5:
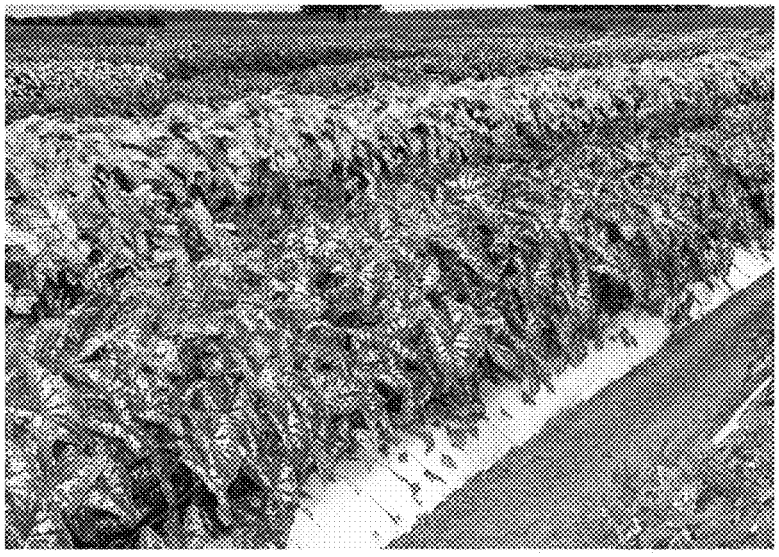

The photograph at the bottom of the third sheet (FIG. 5) is a side perspective view of typical plants of 'WCH OF14-1172' grown in an open production field.

Figure 6:
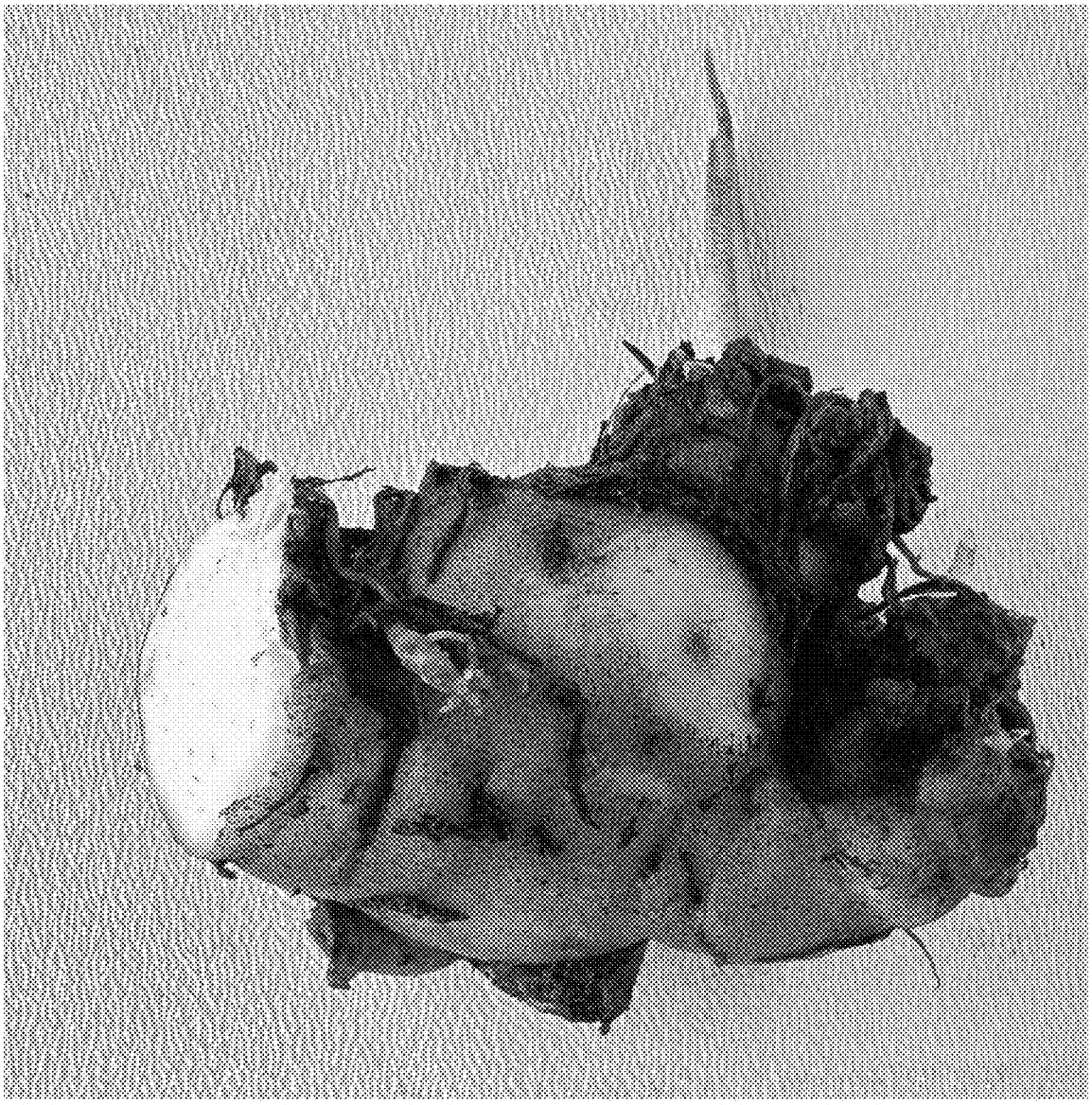

The photograph on the fourth sheet (FIG. 6) is a close-up view of typical freshly-harvested tubers with roots of 'WCH OF14-1172'.

DETAILED BOTANICAL DESCRIPTION

The aforementioned photographs and following observations and measurements describe plants grown in 15-cm containers in a polypropylene-covered shade house (30% light reduction) in Avon Park, Florida and plants grown in ground beds under full sunlight conditions in an outdoor nursery in Crewsville, Florida. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 1,300 μmol. During the production of the outdoor nursery-grown plants, day temperatures ranged from about 29° C. to 35° C., night temperatures ranged from about 23° C. to 26° C. and full sunlight conditions. Plants grown in the shade house were five to six weeks old and plants grown in the outdoor nursery were seven months old when the photographs and the detailed description were taken. In the following description, color references are made to The Royal Horticultural Society Colour Chart, 2001 and 2015 Editions, except where general terms of ordinary dictionary significance are used.

Botanical classification: *Caladium* X *hortulanum* 'WCH OF14-1172'.

Parentage:

*Female, or seed, parent.*—*Caladium* X *hortulanum* 'White Christmas', not patented.

*Male, or pollen, parent.*—*Caladium* X *hortulanum* 'Monument', disclosed in U.S. Plant Pat. No. 27,948.

Propagation:

*Type.*—By "chipping" the tubers.

*Time to initiate roots, summer.*—About seven to ten days at temperatures about 32° C.

*Time to initiate roots, winter.*—About two to three weeks at temperatures about 24° C.

*Tuber description* (*outdoor nursery-grown plants*).—Appearance: Multi-segmented and branched; individual segments are ovate or irregular in shape. Height: About 3.3 cm to 4.2 cm. Diameter: About 4.9 cm to 9.4 cm. Segment height: About 1.7 cm to 2.4 cm. Segment diameter: About 1.7 cm to 2.5 cm. Axillary bud shape: Roughly triangular. Axillary bud height: About 3.3 mm. Axillary bud width: About 3 mm. Texture: Thick, starchy; somewhat brittle. Color: Periderm, freshly-harvested: Close to 199A. Periderm, dried: Close to 200A. Epidermis: Close to 158A to 158B. Cortical tissue: Close to 11D. Axillary buds: Close to 38B. Root description: Relatively thick, fleshy contractile roots with few lateral branches; color, close to NN155D and N155B; actual color of the roots is dependent on substrate composition, water quality, fertilizer type and formulation, substrate temperature and physiological age of roots; root density, moderately dense.

Plant description:

*Plant type*.—Herbaceous perennial; suitable as a potted plant in containers 15-cm to 25-cm and suitable as a landscape plant in shaded areas.

*Plant and growth habit*.—Upright plant habit; intermediate to tall in height; dense, leafy and bushy appearance; vigorous growth habit and rapid growth rate; potted plants finish in saleable form in about five to six weeks after planting tubers; leaf petioles and leaves arise from one or more growing points on tubers; leaf petioles initially upright and leaning outwardly with development.

*Plant height, from soil level to top of foliar plane, shade house-grown potted plants, tubers de-eyed*.—About 26 cm to 33 cm.

*Plant height, from soil level to top of foliar plane, shade house-grown potted plants, tubers not de-eyed*.—About 33 cm to 40.2 cm.

*Plant diameter, shade house-grown potted plants, tubers de-eyed*.—About 24 cm to 31 cm.

*Plant diameter, shade house-grown potted plants, tubers not de-eyed*.—About 29 cm to 31 cm.

*Number of shoots per plant, shade house-grown potted plants, tubers de-eyed*.—About nine to ten seven develop per #1 tuber.

*Number of shoots per plant, shade house-grown potted plants, tubers not de-eyed*.—About four to eight develop per #1 tuber.

*Cataphylls, shade house-grown potted plants*.—Length: About 5 cm to 7 cm. Width: About 1.5 cm. Shape: Elliptic to wedge-shaped. Apex: Acute. Base: Sheathing the stem. Texture, outer and inner surfaces: Smooth, glabrous. Color, outer and inner surfaces: Close to 200A to 200B tinged with close to 185C.

Leaf description:

*Arrangement and type*.—Alternate; simple; fancy-type.

*Length, shade house-grown potted plants, tubers de-eyed*.—About 13.5 cm to 18 cm.

*Length, shade house-grown potted plants, tubers not de-eyed*.—About 15 cm to 24 cm.

*Width, shade house-grown potted plants, tubers de-eyed*.—About 10 cm to 13.8 cm; when flattened, about 12.4 cm to 14 cm.

*Width, shade house-grown potted plants, tubers not de-eyed*.—About 10.6 cm to 17 cm; when flattened, about 11.1 cm to 17.5 cm.

*Shape*.—Broadly ovate with cordate tendencies.

*Apex*.—Acute to acuminate or obtuse.

*Base*.—Sagittate-peltate, cordate.

*Margin*.—Entire; wavy with broad undulations.

*Texture and luster, upper surface*.—Smooth, glabrous; interveinal areas, rugose; dull sheen.

*Texture and luster, lower surface*.—Smooth, glabrous; glaucous around midvein and lateral venation; interveinal areas, rugose; dull sheen.

*Venation pattern*.—Pinnate and palmate.

*Color, shade house-grown potted plants*.—When developing and fully expanded leaves, upper surface: Ground color (interveinal areas): Close to NN155D, 146C, 148D and/or NN137B to NN137C with random flecks, close of 145D or NN155D; random and variable pink blushed areas, close to 56A, 56B and/or 56C. Marginal areas and areas adjacent to the veins: Close to NN137B to NN137C with random flecks, close to 145D and NN155D; edges, close to 187B. Basal notch: Close to 187B. Midvein and lateral venation: Close to 137B. When developing and fully expanded leaves, lower surface: Ground color (interveinal areas): Close to NN155D, 56A, 56B, 191B, 191C, 195C and/or 146C; random and variable pink blushed areas, close to 56A and/or 56B. Marginal areas and areas adjacent to the veins: Close to 191B; edges, close to 187B. Basal notch: Close to 187B. Petiole attachment: Close to N186C. Midvein: Close to 145C and 157A; near petiole attachment, close to 181C to 181D. Lateral venation: Close to 148D and 194B.

*Petioles*.—Aspect: Initially upright and straight and leaning outwardly with development; flexible. Length, shade house-grown potted plants, tubers de-eyed: About 22.5 cm to 32 cm. Length, shade house-grown potted plants, tubers not de- eyed: About 23.5 cm to 37 cm. Diameter, distally, shade house-grown potted plants, tubers de-eyed or not de-eyed: About 4 mm to 5 mm. Diameter, proximally, shade house-grown potted plants, tubers de-eyed or not de-eyed: About 6 mm to 10 mm. Texture: Smooth, glabrous; distally, slightly glaucous, and proximally, glossy. Color, shade house-grown potted plants: Proximally: Close to 203A with occasional stripes, close to N170D and 199C to 199D and tinged with close to 148C and 195B. Distally: Close to N200A with stripes, close to 199C, 199D and/or 148B; just below the leaf junction, close to 148B tinged with close to 181A and 181B with stripes and streaks, close to 200B. Wing length, shade house-grown potted plants: About 6 cm to 10 cm. Wing diameter, shade house-grown potted plants: About 4 mm to 9 mm. Texture and luster, outer and inner surfaces: Smooth, glabrous; glossy. Wing color, shade house-grown potted plants: Outer surface: Close to 195B, N148B to N148C with flecks and streaks, close to 200A. Inner surface: Close to NN155C; colors and patterns from the outer surface are visible on the inner surface.

Inflorescence description: To date, inflorescence development has not been observed on plants of the new *Caladium*.

Pathogen tolerance/resistance: Plants of the new *Caladium* have been observed to have average tolerance to *Pythium* Root Rot and above average tolerance to *Xanthomonas* Leaf Spot. Plants of the new *Caladium* have not been observed to have tolerance/resistance to other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'WCH OF14-1172' as herein illustrated and described herein.

* * * * *